United States Patent
Yamamoto

(10) Patent No.: US 8,939,879 B2
(45) Date of Patent: Jan. 27, 2015

(54) METHOD FOR TRANSPORTING AND FOLDING ARTICLES

(75) Inventor: Yoichiro Yamamoto, Cologne (DE)

(73) Assignee: The Procter & Gamble Company, Cincinnati, OH (US)

( * ) Notice: Subject to any disclaimer, the term of this patent is extended or adjusted under 35 U.S.C. 154(b) by 865 days.

(21) Appl. No.: 13/183,481

(22) Filed: Jul. 15, 2011

(65) Prior Publication Data

US 2012/0015792 A1    Jan. 19, 2012

Related U.S. Application Data

(60) Provisional application No. 61/364,604, filed on Jul. 15, 2010.

(51) Int. Cl.
| | | |
|---|---|---|
| *B31F 1/10* | (2006.01) | |
| *B31F 1/08* | (2006.01) | |
| *A61F 13/15* | (2006.01) | |
| *B65H 45/04* | (2006.01) | |

(52) U.S. Cl.
CPC ..... *A61F 13/15747* (2013.01); *A61F 13/15764* (2013.01); *B65H 45/04* (2013.01); *B65H 2801/57* (2013.01)
USPC ............ 493/440; 493/441; 493/442; 493/356

(58) Field of Classification Search
CPC .................... A61F 13/00987; A61F 13/15707; A61F 13/15747; A61F 13/15764; B65G 47/00; B65H 45/04; B65H 45/16
USPC .......................... 493/356, 358, 440-442, 424
See application file for complete search history.

(56) References Cited

U.S. PATENT DOCUMENTS

| | | |
|---|---|---|
| 4,940,464 A | 7/1990 | Van Gompel et al. |
| 5,092,861 A | 3/1992 | Nomura et al. |
| 5,167,897 A | 12/1992 | Weber et al. |
| 5,246,433 A | 9/1993 | Hasse et al. |
| 5,360,420 A | 11/1994 | Cook et al. |
| 5,569,234 A | 10/1996 | Buell et al. |
| 5,599,335 A | 2/1997 | Goldman et al. |
| 5,643,588 A | 7/1997 | Roe et al. |

(Continued)

FOREIGN PATENT DOCUMENTS

| | | |
|---|---|---|
| EP | 1 595 517 A1 | 11/2005 |
| EP | 1 726 278 A1 | 11/2006 |

(Continued)

OTHER PUBLICATIONS

PCT International Search Report dated Sep. 27, 2011, 10 pages.

(Continued)

*Primary Examiner* — Gloria R Weeks
(74) *Attorney, Agent, or Firm* — Abbey Lopez

(57) ABSTRACT

An apparatus for folding articles advancing in a machine direction including a rotatable roll having a roll surface, at least one protrusion that defines an outermost surface of the roll and at least one pocket that defines an innermost surface of the roll. The apparatus also includes a first and second vacuum conveyor assembly, each comprising two vacuum conveyors. The roll and the vacuum conveyor assemblies are cooperatively configured to fold an article. A method for folding articles by accelerating a portion of the article to create slack in the article, as may be practiced using an apparatus as described.

19 Claims, 12 Drawing Sheets

(56) References Cited

U.S. PATENT DOCUMENTS

| | | | |
|---|---|---|---|
| 5,674,216 A | 10/1997 | Buell et al. | |
| 5,702,551 A | 12/1997 | Huber et al. | |
| 5,897,545 A | 4/1999 | Kline et al. | |
| 5,957,908 A | 9/1999 | Kline et al. | |
| 5,968,025 A | 10/1999 | Roe et al. | |
| 6,107,537 A | 8/2000 | Elder et al. | |
| 6,118,041 A | 9/2000 | Roe et al. | |
| 6,120,487 A | 9/2000 | Ashton | |
| 6,120,489 A | 9/2000 | Johnson et al. | |
| 6,153,209 A | 11/2000 | Vega et al. | |
| 6,410,129 B2 | 6/2002 | Zhang et al. | |
| 6,426,444 B2 | 7/2002 | Roe et al. | |
| 6,586,652 B1 | 7/2003 | Warner et al. | |
| 6,617,016 B2 | 9/2003 | Zhang et al. | |
| 6,627,787 B1 | 9/2003 | Roe et al. | |
| 6,705,453 B2 | 3/2004 | Blumenthal et al. | |
| 6,820,869 B2 * | 11/2004 | Lange et al. | 270/42 |
| 6,825,393 B2 | 11/2004 | Roe et al. | |
| 6,861,571 B1 | 3/2005 | Roe et al. | |
| 6,888,143 B2 | 5/2005 | Vogt et al. | |
| 7,771,336 B2 * | 8/2010 | Shoji et al. | 493/362 |
| 7,955,244 B2 * | 6/2011 | Burns et al. | 493/440 |
| 8,469,869 B2 * | 6/2013 | Yamamoto | 493/442 |
| 8,485,956 B2 * | 7/2013 | Burns et al. | 493/424 |
| 2002/0103468 A1 | 8/2002 | Nakakado et al. | |
| 2003/0233082 A1 | 12/2003 | Kline et al. | |
| 2006/0276320 A1 | 12/2006 | Aiolfi et al. | |
| 2007/0144324 A1 * | 6/2007 | Robert et al. | 83/659 |
| 2009/0094941 A1 | 4/2009 | Burns et al. | |
| 2009/0098995 A1 | 4/2009 | Burns et al. | |
| 2012/0238431 A1 * | 9/2012 | Sablone et al. | 493/441 |

FOREIGN PATENT DOCUMENTS

| | | |
|---|---|---|
| EP | 1 941 854 A2 | 7/2008 |
| WO | WO 95/19752 A2 | 7/1995 |
| WO | WO 2008/001209 A2 | 1/2008 |
| WO | WO 2009/032995 A1 | 3/2009 |
| WO | WO 2009/083788 A1 | 7/2009 |

OTHER PUBLICATIONS

PCT International Search Report dated Oct. 28, 2011, 12 pages.
U.S. Appl. No. 13/183,483, filed Jul. 15, 2011, Yoichiro Yamamoto.
U.S. Appl. No. 13/183,486, filed Jul. 15, 2011, Yoichiro Yamamoto.
U.S. Appl. No. 13/183,490, filed Jul. 15, 2011, Yoichiro Yamamoto.
U.S. Appl. No. 12/203,339, filed Sep. 3, 2008, John Glasgow Burns, Jr.
U.S. Appl. No. 13/051,210, filed Mar. 18, 2011, Yoichiro Yamamoto.
PCT International Search Report dated Aug. 30, 2011, 11 pages.

* cited by examiner

METHOD FOR TRANSPORTING AND FOLDING ARTICLES

CROSS REFERENCE TO RELATED APPLICATION

This application claims the benefit of U.S. Provisional Application No. 61/364,604, filed on Jul. 15, 2010.

FIELD OF THE INVENTION

The present disclosure relates to methods and apparatuses for manufacturing articles, and more particularly, to an improved transfer conveyor and folding drum for transferring, folding, and optionally seaming articles of different sizes.

BACKGROUND OF THE INVENTION

Disposable absorbent articles, such as diapers, pull-on diapers, training pants, adult incontinence pads, wipes, facial tissue, toilet tissue, napkins, paper towels and the like are often manufactured and/or packaged on a high-speed production line where individual articles may move along a production path at a speed of hundreds of meters per minute, and manufacturers of articles are continually trying to increase manufacturing speed. However, in order to increase the speed of a manufacturing process, larger, more powerful drive motors are typically required to increase the operational speed of the various components in the process. Such motors can be costly and take up an undesirable amount of floor space in the manufacturing facility. Further, increasing the roll speed may undesirably affect the timing of the upstream and/or downstream processes, for example, by increasing the precision needed to synchronize the upstream and/or downstream processes with the new, faster roll speed.

In conventional manufacturing processes, it is not uncommon for rolls, sometimes referred to as drums or cylinders, to be used to transport articles from one component or portion of the process to another. Known folding rolls and/or transport rolls typically have a substantially uniform, two-dimensional, curved surface, and an article disposed on the surface of such a roll is generally disposed in a "flat-out" configuration on the roll surface (i.e., no slack in the article which could cause bunching, wrinkles, looseness, or the like). Thus, the number of flat-out articles of a particular length that can be accommodated by a roll may be directly determined by the circumference of the roll. For example, a conventional folding drum having a circumference of 600 mm can accommodate no more than three articles having a length of 200 mm each, assuming the articles do not overlap one another. If the length of each article is increased, for example to 300 mm, and the circumference of the roll is unchanged, then only two articles can be accommodated by the roll per revolution, assuming articles do not overlap. Conversely, reducing the size of the articles, for example to 100 mm each, without changing the circumference or speed of the roll may permit the roll to accommodate up to 6 articles per revolution. While it may be possible to increase the size of the roll, replacing a roll can be expensive and the larger size may undesirably affect the relative positions and/or timing of other components in the manufacturing process. Increasing the speed of the roll may increase the rate at which articles are processed, but, as pointed out above, it typically requires providing a larger motor, which may not be desirable. In addition, if variable speed servo motors are used, increasing the power of the motor may increase the inertia of the motor and potentially offset any speed increases desired. Decreasing the size of an article may increase the rate at which the articles can be processed. But decreasing the size of an article may not be a practical option for certain articles such as disposable diapers, training pants, or other articles that are typically manufactured in particular sizes to fit different sizes of wearers.

Accordingly, it would be desirable to provide a process and apparatus for increasing the number of articles transported on a folding drum without increasing the size or speed of the drum.

SUMMARY OF THE INVENTION

In some aspects, the present disclosure relates to a method for folding an article. The method may comprise transferring a leading edge portion of the article from a first carrier moving at a first speed to a movable surface of a first transfer apparatus moving at the first speed. The method may comprise slowing the leading end portion to a second speed such that slack is formed in the article. The method may comprise transferring a trailing end portion of the article to the moving surface of the first transfer apparatus at the first speed. The method may comprise accelerating the leading end portion of the article to a third speed that is greater than the first speed. The method may comprise accelerating the trailing end portion of the article to a third speed that is greater than the first speed. The method may comprise accelerating the trailing end portion of the article to the third speed. The method may comprise transferring the article to a rotating folding drum moving at the third speed. The folding drum may comprise at least one pocket. The folding drum may comprise at least one protrusion. The method may comprise transferring the leading end portion of the article to a movable surface of a second transfer apparatus. The method may comprise transferring the leading end portion of the article to a movable surface of a third transfer apparatus. The method may comprise accelerating the leading end portion to the third speed. The method may comprise transferring the leading end portion to the folding drum at the third speed such that the leading end portion and the trailing end portion are arranged in a face-to-face relationship to form a folded article.

The method may comprise joining the leading end portion and the trailing end portion together. The leading end portion and the trailing end portion may be joined permanently or refastenably. The article may be a disposable absorbent article. The disposable absorbent article may comprise a first waist region. The first waist region may correspond to the leading end portion. The disposable absorbent article may comprise a rear waist region. The rear waist region may correspond to the trailing end portion. The waist regions may each include at least one fastener. The fasteners of the waist regions may be joined together. The fasteners of the waist regions may be joined together to form a pre-fastened pant.

The leading end portion may be transferred to a first protrusion on the folding drum. The trailing end portion may be transferred to a second protrusion on the folding drum. The slack may be disposed in a pocket between the first and second protrusions. The protrusion may define an outer surface of the folding drum. The article may comprise opposing end edges. A distance between the opposing end edges as measured on the outer surface of the folding drum may be less than the distance between the opposing end edges when the article is in a flat-out configuration. The distance between the opposing end edges as measured on the outer surface of the folding drum may be at least about 10% less than the distance between the opposing end edges when the article is in a flat-out configuration.

The second transfer apparatus may include a first vacuum conveyor. The second transfer apparatus may comprise a second vacuum conveyor. The first vacuum conveyor may be positioned proximate to a surface of the folding drum. The first vacuum conveyor may receive the leading end portion from the surface of the folding drum at the third speed. The first vacuum conveyor may transfer the leading end portion to the second conveyor at the third speed. The second vacuum conveyor may decelerate the leading end portion to the fourth speed. The first and second vacuum conveyors may share a common element.

The third transfer apparatus may include a third vacuum conveyor and a fourth vacuum conveyor. The third vacuum conveyor may be positioned proximate to the movable surface of the second transfer apparatus. The third vacuum conveyor may receive the leading end portion from the movable surface of the second transfer apparatus at the fourth speed. The third vacuum conveyor may accelerate the leading end portion to the third speed. The third vacuum conveyor may transfer the leading end portion to the fourth vacuum conveyor at the third speed. The fourth vacuum conveyor may transfer the leading end back to the folding drum at the third speed. The third and fourth vacuum conveyors may share a common element.

At least one of the second and third transfer apparatuses may be respositionable. At least one of the second and third transfer apparatuses may be respositioned to vary the distance between the movable surface of the second transfer apparatus and the movable surface of the third transfer apparatus. The fourth speed may be zero. The leading and trailing end portions may be aligned in a face-to-face configuration. A first set of belts may transfer the leading end portion of the article from the first carrier to the folding drum. A second set of belts may transfer the trailing end portion of the article from the first carrier to the folding drum.

In some aspects, the present disclosure relates to an apparatus for transferring articles in a machine direction from a first carrier moving at a first speed to a folding drum moving at a second speed that is greater than the first speed, and folding the articles. Each article may have a leading end portion and a trailing end portion. The apparatus may comprise a first carrier moving at a first speed. The first carrier may be configured to transfer a leading end portion of the article to a movable surface of a first transfer apparatus moving at the first speed. The transfer apparatus may comprise a first transferring surface configured to receive the leading end portion of each article from the first carrier and transport the leading end portion to the folding drum. The first transferring surface may be mechanically coupled to a first drive motor that advances the first transferring surface in the machine direction. The first drive motor may be configured to advance the first transferring surface at the first speed when the leading end of each article is transferred from the first carrier to the first transferring surface. The first drive motor may be configured to slow the first transferring surface to accumulate slack in the article. The first drive motor may be configured to accelerate the first transferring surface back to the second speed such that the leading end of the article is transferred to the folding drum at the second speed.

The apparatus may comprise a second transferring surface configured to receive the trailing end portion of each article from the first carrier. The second transferring surface may be configured to transport the trailing end of each article to the folding drum. The second transferring surface may be mechanically coupled to a second drive motor. The second drive motor may advance the second transferring surface in the machine direction. The second drive motor may be configured to advance the second transferring surface in the machine direction at the first speed when the trailing end of each article is transferred from the first carrier to the second transferring surface. The second drive motor may be configured to accelerate the second transferring surface to the second speed such that the trailing end of each article is transferred to the folding drum at the second speed.

The apparatus may comprise a rotatable roll. The rotatable roll may comprise a roll surface. The roll surface may at least one protrusion. The roll surface may include at least one pocket. The apparatus may comprise a peel assembly. The apparatus may comprise a folding assembly. Each of the peel assembly and the folding assembly may include at least one movable surface. The peel assembly may be configured to remove the leading end portion of the article from the folding drum. The peel assembly may be configured to transfer the leading end portion to a folding assembly. The folding assembly may be configured to receive the leading end portion from the peel assembly. The folding assembly may be configured to transfer the leading end to the folding drum. The leading end portion and the trailing end portion may be arranged in a face-to-face relationship. The leading end portion and the trailing end portion may form a folded article.

DETAILED DESCRIPTION OF THE INVENTION

Definitions

Figure 1:
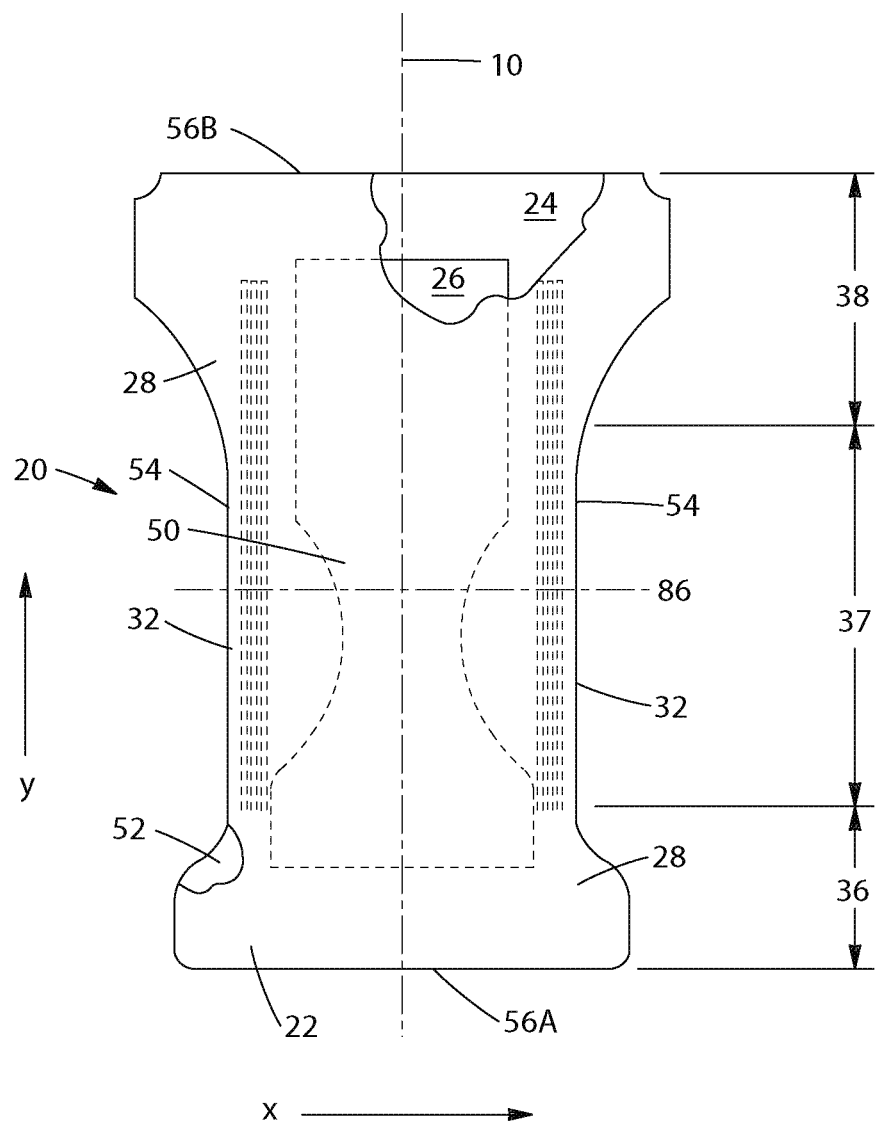
FIG. 1 is a top, plan view of a disposable absorbent article.

"Absorbent article" means a consumer product whose primary function is to absorb and retain soils and wastes, such as devices which are placed against or in proximity to the body of the wearer to absorb and contain the various exudates discharged from the body. Nonlimiting examples of absorbent articles include diapers, training pants, pull-on pant-type diapers, refastenable diapers or pant-type diapers, incontinence briefs and undergarments, diaper holders and liners, feminine hygiene garments such as panty liners, absorbent inserts, and the like.

"Aligned" means an article in a bifold configuration having an average CD accuracy and an MD accuracy of less than or equal to 3 mm, when measured according to the Alignment Test described in copending U.S. Publication. No. 2009/0098995, titled "System For Bifolding An Absorbent Article," filed by Burns, et al.

"Bifold" means folding an article into two portions. For example, bifolding a disposable diaper may be accomplished by bringing the leading end and the trailing end of the diaper together in a face-to-face configuration on a production line as the article moves in the machine direction of travel, such that the diaper is folded along a fold line into two substantially equal portions. As used herein, a "fold line" is the portion of an article about which the article is folded. The fold line typically extends from one side edge to the opposing side edge in the crotch region and, in certain embodiments, may correspond to the lateral centerline of the article. In certain embodiments, the leading end edge and trailing end edge of an article may be aligned after the article is folded.

"Diaper" or "taped diaper" mean disposable absorbent articles having an initial front waist region and an initial back waist region that are not fastened, pre-fastened, or connected to each other as packaged, prior to being applied to the wearer. A taped diaper is folded about the lateral centerline with the interior of one waist region in surface to surface contact with the interior of the opposing waist region without fastening or joining the waist regions together. Suitable examples of taped diaper configurations are disclosed in U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571.

"Disposable" means articles that are generally not intended to be laundered or otherwise restored or reused as absorbent articles (i.e., they are intended to be discarded after a single use and may be recycled, composted or otherwise discarded in an environmentally compatible manner).

"Disposed" means an element(s) is formed (joined and positioned) in a particular place or position as a macro-unitary structure with other elements or as a separate element joined to another element.

"Engage," when used in the context of transferring an article from one carrier to another or from a portion of one carrier to another portion of the same carrier, means coming into close proximity (e.g., <10 cm, up to and including physical contact) such that an engaging force (e.g., suction) present at the surface of the carrier can be applied to an article.

"Holding an article to the surface of a roll" and variations thereof mean employing a holding force to one or more portions of an article in order to join the article at least temporarily to the surface of a roll such that the article is inhibited from traveling in a direction substantially orthogonal to the surface of the roll without reducing or removing the holding force and/or employing a peel-force. This definition is equally applicable to conveyors, e.g., one or more of the conveyor assemblies described hereinbelow.

"Joined" means configurations whereby an element is directly secured to another element by affixing the element directly to the other element and to configurations whereby an element is indirectly secured to another element by affixing the element to intermediate member(s) which in turn are affixed to the other element.

"Longitudinal" means a direction running substantially perpendicular from a waist edge to an opposing waist edge of an absorbent article when the article is in a flat out, uncontracted state, or from a waist edge to the bottom of the crotch in a bifolded article. Directions within 45 degrees of the longitudinal direction are considered to be "longitudinal." "Lateral" refers to a direction running from a longitudinal edge to an opposing longitudinal edge of an article and generally orthogonal to the longitudinal direction. Directions within 45 degrees of the lateral direction are considered to be "lateral."

"Machine direction" ("MD") means the direction that is parallel to the direction of travel of an article or article element as it is processed in the forming apparatus. In a folding process such as a bifolding process, it may be possible to have more than one machine direction when an article is undergoing simultaneous processes. In other words, a manufacturing line may have an overall machine direction, but an article may travel in directions other than the overall machine direction as it passes through various process along the manufacturing line. For example, an article having a trailing end portion and a leading end portion, each portion being attached to the surface of a different roll and/or conveyor, may travel in two different directions simultaneously. In this example, both directions of travel may be considered the machine direction. The "cross machine direction" or "cross direction" ("CD") refers to the direction perpendicular to the machine direction and in the plane generally defined by the article or article element.

"Mechanically coupled" means two or more components that, directly or indirectly, act cooperatively to form a mechanism. For example, an electric motor that drives the motion of a gate is said to be mechanically coupled to the gate. The mechanism of operation that mechanically couples the component may be any one of a number of commonly known couplers, including but not limited to: having a shaft extending between the components; a universal joint; a transmission; a linkage; a sprocket and chain; a gear head on one of the components; a gear box; a belt and pulley combination; a clutch mechanism; a spring member; a slider; a pivot; or other known forms of coupling two elements may also be considered mechanical coupling.

"Mechanically secured" means holding an object in place by a mechanical means. For example, a web of material or an absorbent article held to the outer surface of a roll with clips is considered to be mechanically secured. Conversely, holding a web of material or an absorbent article to the surface of a roll with vacuum pressure or centrifugal force is not an example of being mechanically secured.

"Peel force" means the force applied to an object in a direction that is substantially perpendicular to the plane of the surface on which the object rests. A force applied in a direction within 45° of the perpendicular direction may be considered a peel force.

"Training pant(s)" or "pant(s)" mean disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by any suitable technique including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened, front waist fastened, rear waist fastened). Suitable examples of pants in various configurations are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082.

"Vacuum" and "vacuum pressure" mean a pressure of less than 13000 Newtons per square meter.

For ease of understanding, portions of the following description may be exemplified in terms of a disposable absorbent article. However, it is to be understood that while one or more particular examples recited herein may refer to a diaper or training pant, the present invention is not limited to such articles. The folding and transfer system described herein may, in fact, be practiced in any situation where an article exhibiting the characteristics described herein is required. Examples of other articles include hard surface cleaning wipes or pads; pre-moistened cloths; paper towels;

dryer sheets and dry-cleaning clothes; adult incontinence briefs and undergarments; feminine hygiene garments such as panty liners, absorbent inserts, and the like; toilet paper; tissue paper; personal cleaning wipes or clothes such as baby wipes or facial wipes; packaging components and substrates and/or containers for laundry detergent and coffee, which may be produced in pellets or pouches and may be manufactured in a converting or web process; or even discrete products produced at high speed such as high-speed bottling lines, cosmetics, razor blade cartridges, and disposable consumer batteries.

FIG. 1 shows a partial cut-away view of a diaper 20 shown in a flat-out, uncontracted state (e.g., with no elastic induced contraction). The diaper 20 may include a body-faceable, liquid pervious topsheet 22 (i.e., faces and/or contacts the body of a wearer when worn as intended); a clothing-faceable, liquid impervious backsheet 24 joined with the topsheet 22 (i.e., faces and/or contacts the clothing of a wearer when worn as intended); an absorbent core 26 positioned between the topsheet 22 and the backsheet 24; side panels 28; and leg cuffs 32. The diaper 20 may further include an outer surface 52 opposed to the inner surface 50, a first waist region 36, a second waist region 38 opposed to the first waist region 36, and a crotch region 37 positioned between the first waist region 36 and the second waist region 38. The diaper 20 may also include longitudinal edges 54, a first end edge 56A corresponding to the first waist region 36, and an opposing second end edge 56B corresponding to the second waist region 38. The diaper 20 may include a longitudinal centerline 10 positioned midway between the longitudinal side edges 54 and a lateral centerline 86 positioned midway between opposing end edges 56A and 56B and orthogonal thereto. The end edges 56A and 56B may be substantially equal in width, as measured from opposing longitudinal side edges 54 to the longitudinal centerline 10, or length, as measured from opposing end edges 56A and 56B to the lateral centerline 86, in order to facilitate folding of the diaper 20, but need not necessarily be so. According to the methods and apparatuses disclosed herein, the diaper 20 may be folded about the lateral centerline 86 such that the first waist region 36 and the second waist region 38 are positioned in a face-to-face relationship along the inner surface 50 (e.g., in a bifolded configuration). A folded diaper according to certain embodiments may have the first end edge 56A and the second end edge 56B aligned. A folded diaper according to certain embodiments may have the longitudinal side edges 54 partially or entirely aligned (e.g., the longitudinal side edges 54 may be aligned only in those areas that are visible to a consumer and/or are to be permanently joined together).

Figure 2:
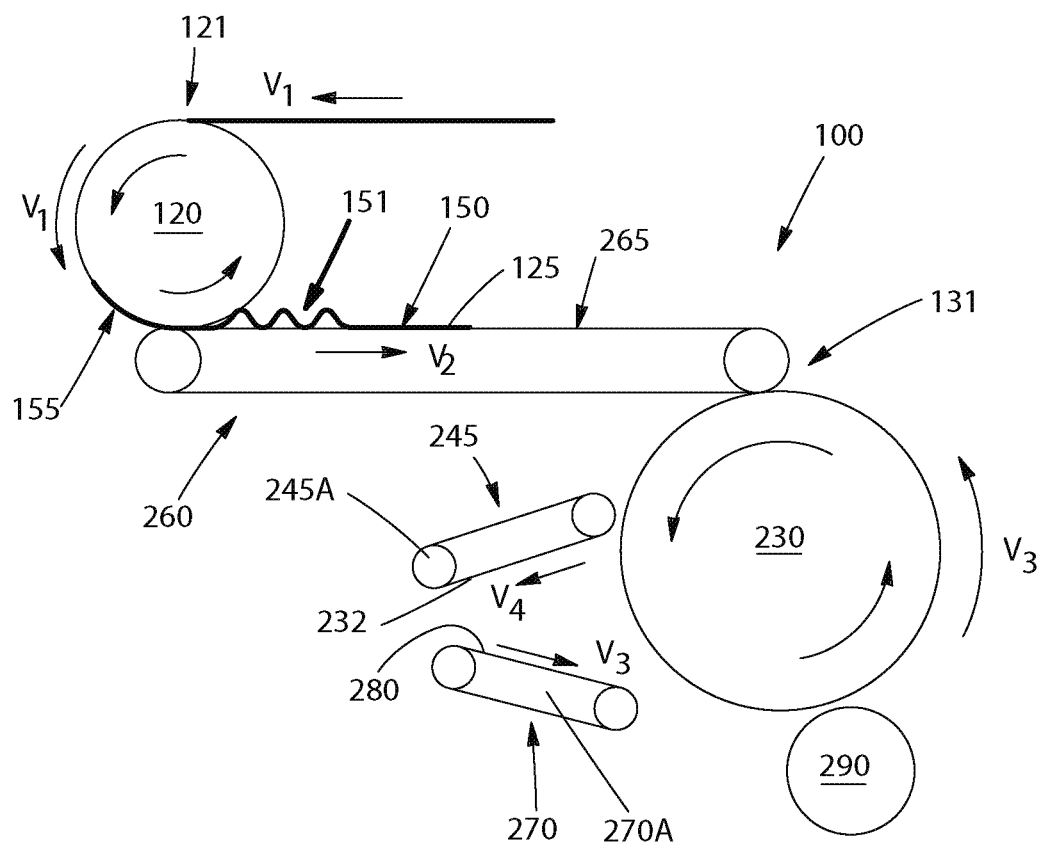
FIG. 2 is a schematic view of an embodiment of the method and apparatus disclosed herein.

FIG. 2 shows an exemplary process 100 for transferring and folding an article 125 such as the diaper 20 shown and described in FIG. 1. Arrows are provided to indicate the direction of movement of particular components in the process 100. As illustrated in FIG. 2, an article 125 may be transported to the infeed 121 of a rotating first carrier 120 travelling at a first speed $V_1$. In the exemplary embodiment shown in FIG. 2, the first carrier 120 is depicted as being a roll, but it is to be appreciated that the first carrier 120 may be replaced with a suitable conveyor, or any other suitable carrier known in the art that is configured to provide an endless moving surface. The surface of the first carrier 120 may be configured to apply a holding force to the absorbent article 125 or portion thereof to help maintain the article 125 in a desired position and/or configuration. For example, the first carrier 120 may include a foraminous surface through which vacuum suction can be provided to hold the article 125 or article portions (e.g., side panels, waist region, ears, and/or fasteners) in place. In certain embodiments, the first carrier 120 may use a mechanical means such as clips or clamps to hold the article 125 or article portions in place. The method used to provide the holding force is not particularly limited as long as it does not undesirably interfere with the process 100. After being received by the first carrier 120, the absorbent article 125 is carried around the rotating surface of the first carrier 120 toward the transfer apparatus 260 at speed $V_1$. Upon reaching the outfeed of the first carrier 120, the leading end 150 of the absorbent article 125 is transferred to the moving surface 265 of the transfer apparatus 260 at speed $V_1$. The leading end portion 150 is the portion of the article 125 positioned downstream of the trailing end portion 155 (i.e., the leading end portion will enter a particular manufacturing process or sequence of processes before the trailing end portion). Before, during, or after transfer of the leading end portion 150 of the absorbent article 125 to the moving surface 265 of the transfer apparatus 260, the holding force exerted by the first carrier 120, if any, may be reduced and/or removed.

Figure 3:
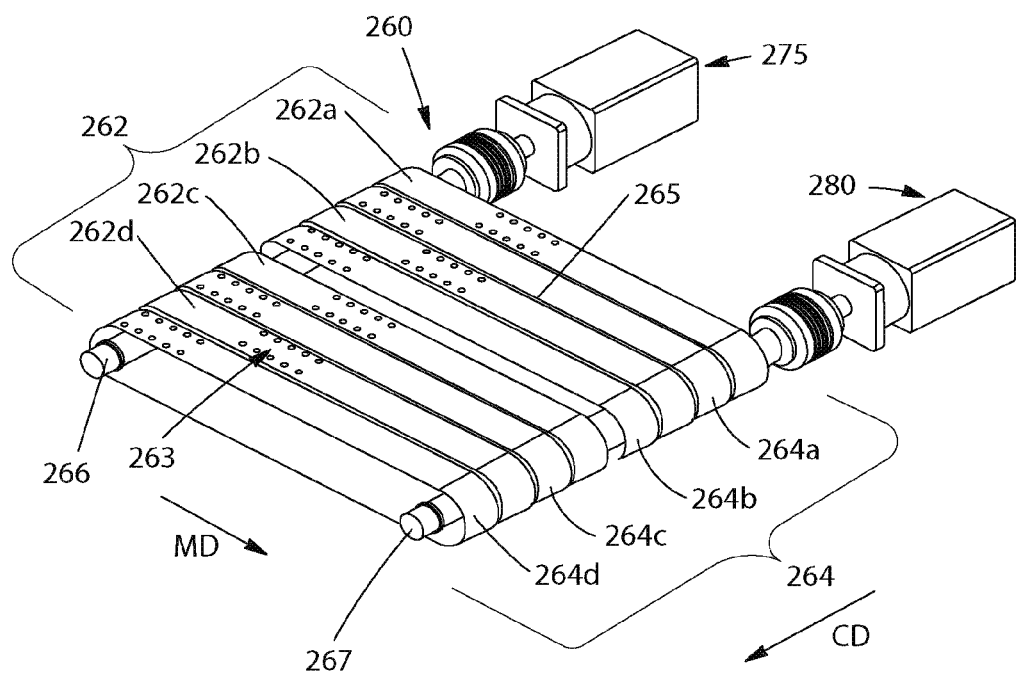
FIG. 3 is a perspective view of an embodiment of a transfer apparatus.

FIG. 3 shows an exemplary embodiment of a transfer apparatus 260 suitable for use herein. As shown in FIG. 3, the transfer apparatus 260 may be a conveyor with a belt configured in an endless loop to provide a movable surface 265. The movable surface 265 may include a first set of four individual belts 262a, 262b, 262c, 262d arranged in an alternating relationship with a second set of four individual belts 264a, 264b, 264c, 264d to form a substantially flat moveable surface. It is to be understood that any number of individual belts (e.g., 2, 3, 5, 6, 7) or sets of belts may be used, as desired. For example, the transfer apparatus 260 may be configured to include 3 or even 4 or more sets of belts to accommodate a variety of cycle rates (e.g., two articles per complete cycle, one and one-half articles per cycle, or 1 article per cycle). The individual belts 262a-d, 264a-d may be the same size or different sizes, as long as the overall size of the set of belts 262, 264 is sufficient to suitably accommodate the desired article size. For example, each set of belts 262, 264 may be sized in the MD to accommodate the longest article in the line-up of absorbent articles provided by a manufacturer. In certain embodiments, the transfer apparatus 260 may transfer two articles each time the endless belt completes a full rotation around the loop, and may be referred to as a so-called "two-up" belt. The width of an individual belt or set of belts is not particularly limited as long as the width of each set of belts 262, 264 in the CD is sufficient to suitably accommodate the desired absorbent article sizes being produced. The individual belts 262a-d, 264a-d in each set of belts 262, 264 cooperatively function to advance a portion of an absorbent article in the MD without inhibiting the advancement of the remaining portions of the article. Thus, in certain embodiments, it may be desirable to hold a portion of the article to the surface or a portion of the surface of one or more of the belts 262a-d, 264a-d. For example, one or more of the belts 262a-d, 264a-d may be configured with one or more openings 263 that extend through the belt 262a-d, 264a-d to permit vacuum to be applied to an article or article portion disposed on the belt. It may be desirable, in certain embodiments, to configured the belts 262a-d, 264a-d such that the holding force (e.g., vacuum) does not undesirably inhibit the advancement of the article portion(s) disposed thereon (e.g., by not placing holes 263 in portions of the belt 262a-d, 264a-d or by the intermittent application of vacuum).

Each set of belts 262, 264 may be driven independently by a drive motor 275, 280 or any other suitable prime mover known in the art (e.g., a variable speed, linear servo motor). A suitable example of a drive motor is a programmable, variable speed, linear servo motor configured such that the coil and magnet assembly of the motor do not make contact, which reduces the amount of dust and/or other particulate contamination generated by the motor during operation and makes the motor more suitable for environments where cleanliness is desired (e.g., when making sanitary disposable articles that are used on or near skin) or where vacuum systems are utilized. In certain embodiments, one or more of the motors may be a constant speed motor. Each drive motor 275, 280 is mechanically coupled to its respective set of belts 262, 264, for example, by a shaft 266, 267 and one or more pulleys. In certain embodiments, each shaft may also be configured to function as a so-called "idler pulley" for the opposite set of driven belts, for example, by permitting the opposing set of belts to ride on a freely rotating (i.e., undriven) pulley mounted to the shaft with a roller bearing. For example, shaft 266 may be used to drive individual belts 262a-d, but function as an idler pulley for individual belts 264a-d.

Figure 4:
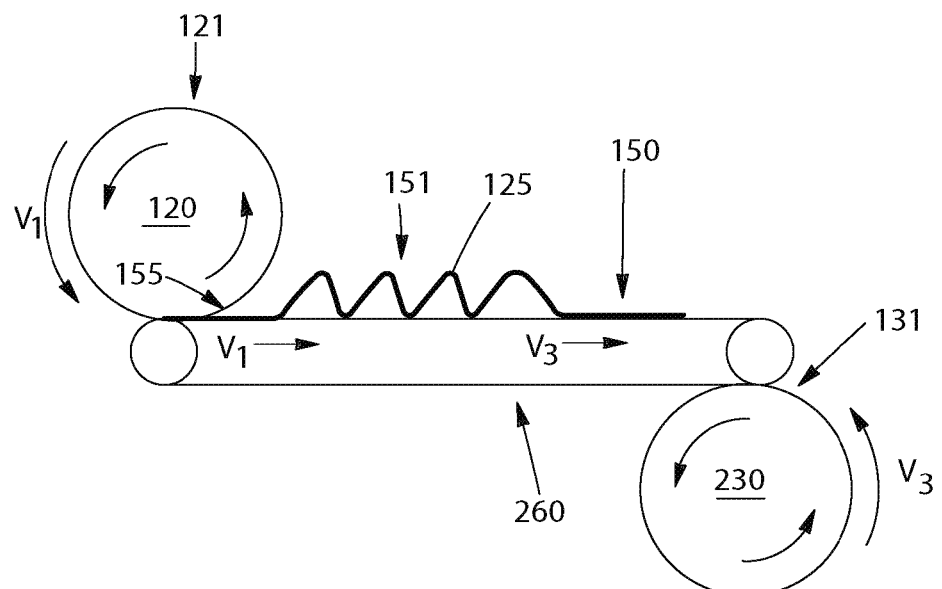
FIGS. 4-5 are schematic views of an embodiment of the method and apparatus disclosed herein.
Figure 5:
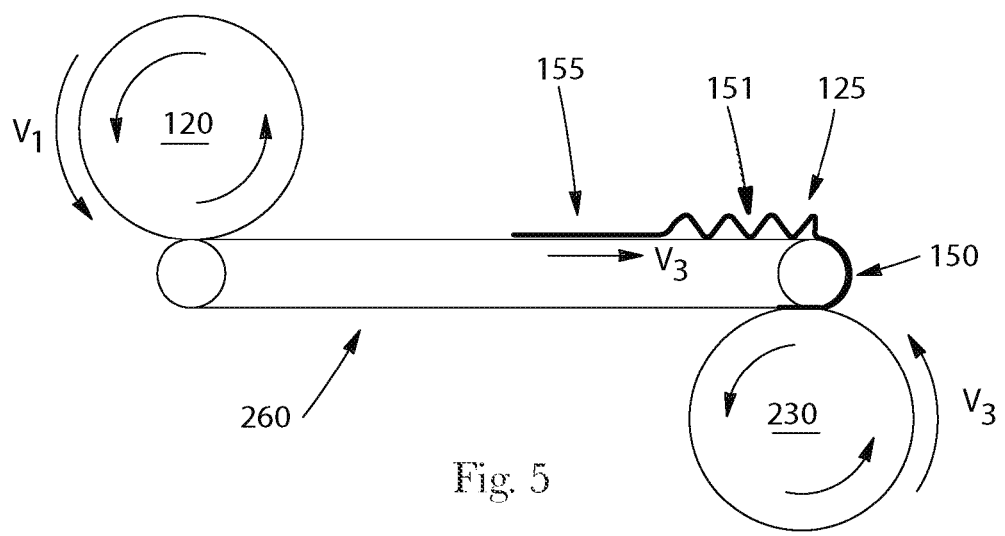

In certain embodiments, as the leading end 150 of the absorbent article 125 approaches the transfer apparatus 260 at a first speed $V_1$, the leading end 150 may be engaged by a first set of belts such as, for example, the first set of belts 264 shown in FIG. 3 by applying a peel force to the leading end 150. The first set of belts may then transport the leading end 250 away from the first carrier 120 toward the infeed 131 of the folding drum 230 in the MD at a second speed $V_2$, which is slower than the first speed $V_1$. Because the rate at which the leading end 150 is being carried away from the first carrier 120 is slower than the rate at which the absorbent article 125 is being fed to the transfer apparatus 260 (i.e., $V_2<V_1$), slack 151 may tend to accumulate in the portion of the article 125 between the trailing end 155 and the leading end 150 ("middle portion"). While the leading end 150 continues to advance in the MD toward the folding drum 230 at the second slower speed $V_2$, more of the absorbent article 125 is fed onto the transfer apparatus 260 at the first speed $V_1$, which causes further accumulation of slack 151 in the article 125, as shown in FIG. 4. Eventually, the trailing end 155 of the absorbent reaches the outfeed 122 of the first carrier 120 and is engaged by a second set of belts such as, for example, the second set of belts 262 shown in FIG. 3 at the first speed $V_1$. In certain embodiments (e.g., before, during, or after the transfer of the trailing end 155 to the second set of belts), the first set of belts may be accelerated to a third speed $V_3$, which is greater than the first speed $V_1$, such that the speed of the leading end 150 is matched with the speed of the folding drum 230. Accelerating the leading end 150 of the article 125 to the third speed $V_3$ will cause some of the slack 151 in the article 125 to be removed, but in certain embodiments, at least some of the slack 151 is still present when the middle portion of the article 125 is transferred to the folding drum 230. The trailing end 155 may be accelerated to the third speed $V_3$ before all of the slack 151 is removed from the article 125. Thus, when the article 125 is transferred to the folding drum 230, at least some slack 151 remains in the article 125.

The leading end 150 of the absorbent article 125 may be transferred to the folding drum 230 at the third speed $V_3$, as described above, and secured to the surface of the folding drum 230. When the absorbent article 125 is in the form of a disposable diaper, pant, or the like, the absorbent article 125 may be transferred to the folding drum 230 such that the topsheet of the absorbent article 125 is facing outward away from the surface 231 of the folding drum 230 and the opposing backsheet of the absorbent article 125 is held against the surface 231 of the folding drum 230. The folding drum 230 may be configured to rotate at a constant or variable speed. The rotational speed and size of the folding drum 230 may be selected to provide a particular line speed and/or article handling capability, as desired. For example, the embodiment shown in the FIG. 6 utilizes a so-called "3-up drum" (i.e., a drum capable of accommodating three articles at once). Thus, for each full rotation of the folding drum 230 three articles (e.g., 125A, 125B, and 125C) are folded. In certain embodiments of a 3-up drum, each folding cycle includes folding one article, and for each cycle the folding drum may rotate between 118° and 122°, and in some instances, the drum rotates 120° for each cycle. In certain embodiments, the drum may be a 5-up drum, i.e., capable of accommodating five article at once, and may rotate between 70° and 74° for each cycle, and in some instances, 72°. In certain embodiments, other size folding drums may be selected, as desired. While the figures may illustrate the first carrier 120 and the folding drum 230 positioned on opposite sides of the transfer apparatus 260, it is to be appreciated that the embodiments where the first carrier 120 and the folding drum 230 are positioned on the same side of the carrier, for example, as depicted in copending U.S. Ser. No. 61/364,626, titled Method And Apparatus For Transferring Articles Of Different Sizes, filed by Yamamoto, et al., on Jul. 15, 2010.

Figure 6:
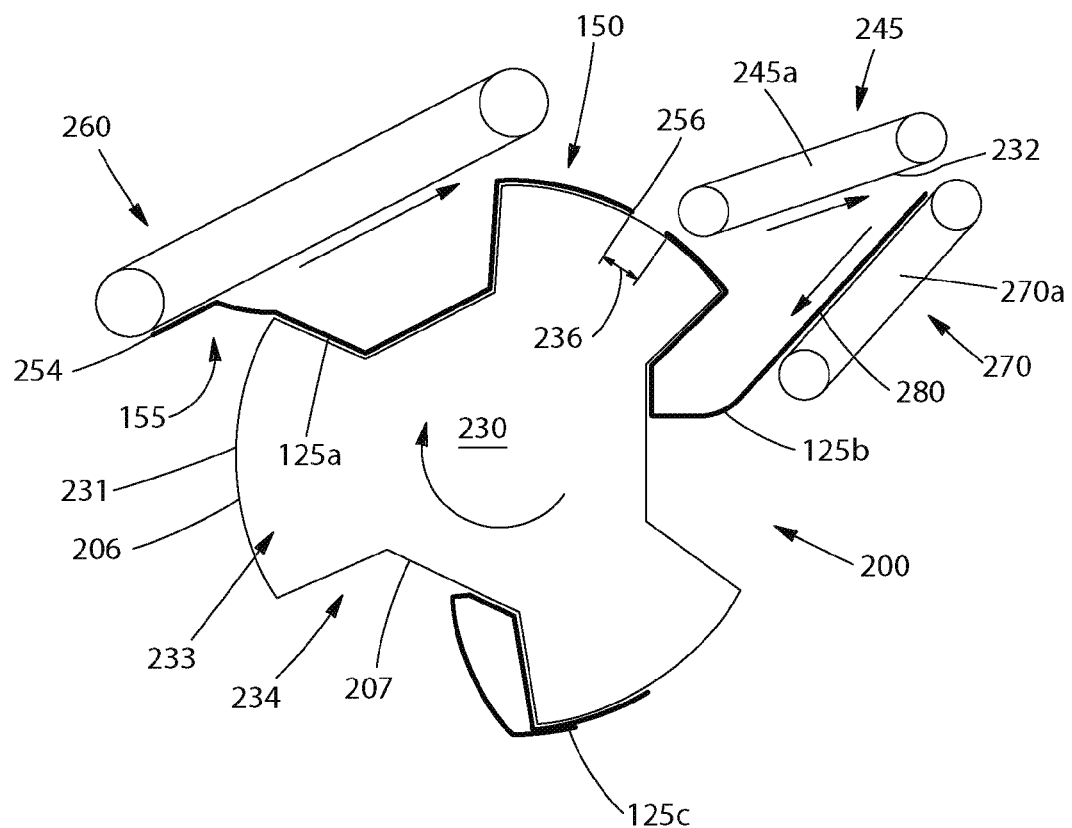
FIG. 6 is a schematic view of an embodiment of the method and apparatus disclosed herein.
Figure 13:
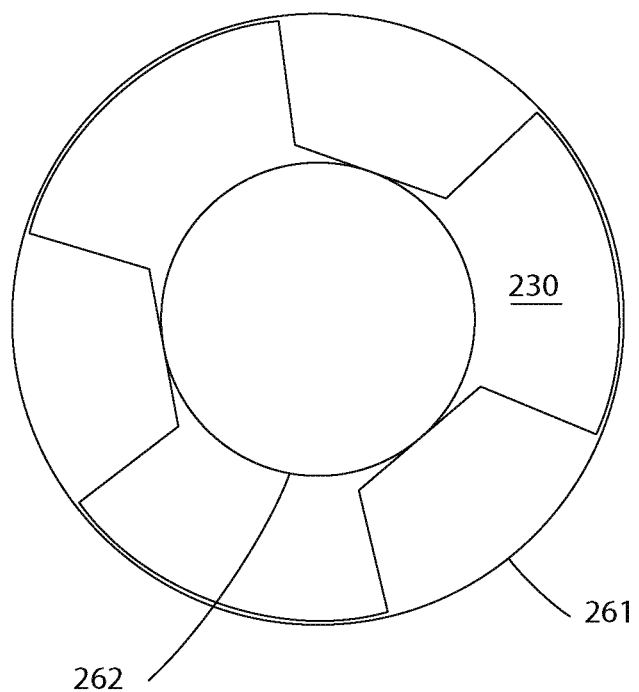
FIG. 13 is a schematic view of an embodiment of a folding drum.

FIG. 6 shows an exemplary embodiment of a folding process 200. The folding process 200 includes a folding drum 230 whose surface 231 is defined by an alternating series of pockets 234 and protrusions 233. Some or all of the pockets 234 and/or protrusions 233 may extend the full width of the surface 231 of the folding drum 230 in the CD, such that the profile of the folding drum 230 appears "gear-like." In certain embodiments, some or all of the pockets 234 and/or protrusions 233 may extend only partially across the folding drum 203 in the CD. The protrusions 234 and/or pockets 233 may be configured to hold the article 125 to the surface 231 of the folding drum, for example, with vacuum. Suitable folding drums 230 for use herein may include any number of protrusions 233 and/or pockets 234, as desired. It is to be understood that the terms protrusion 233 and pocket 234 are relative terms, which are used to conveniently describe the unique, contrasting surface features of the folding drum 230 disclosed herein. The protrusions 233 and pockets 234 may be uniformly sized such that all the pockets are sized the same and/or all of the protrusions are sized the same. Alternatively, some or all the protrusions and/or pockets may be of different sizes. Suitable examples of pockets sizes include a depth (i.e., the distance that the pocket 234 extends away, orthogonally, from the outermost surface of a protrusion 233) of between 10 and 150 mm, 20 and 100 mm, 30 and 80 mm, or even 60 mm. While not particularly limited, it is important to size the pockets according the article and/or portion of the article to be placed in the pocket. The protrusions 233 may define the outermost portion 206 of the surface 231 and the outer circumference 261 of the folding drum 230, as shown in FIG. 13, while the pockets 234 define an innermost portion 207 of the surface 231 and an inner circumference 262. The number of protrusions 233 and pockets 234 present on the folding drum 230 depends on the number of articles to be accommodated by the folding drum 230 (e.g., at least one pocket 234 and at least one protrusion 233 may be required for each article to be accommodated). The protrusions 233 and/or pockets 234 may have relatively uniform surfaces (e.g., smooth). But in certain embodiments, some or all of the pockets 234 and/or protrusions 233 may include surface features such as corrugations, fingers, channels, rough portions, smooth portions, raised portions, lowered portions and the like, for example, to aid in holding and/or transferring an article 125 to and/or from the surface 231 of the folding drum 230.

In certain embodiments, it may be desirable to transfer the leading end 150 of an article 125 from the transfer apparatus 260 to a protrusion 233 on the folding drum 230. As the folding drum 230 rotates, a protrusion 233 will become positioned proximate to the transfer apparatus 260 such that the leading end 150 of the absorbent article 125 can be transferred to the protrusion 233. After the leading end 150 is transferred to the protrusion 233, a holding force (e.g., vacuum) may be applied to the leading end 150 to secure it to the surface 231 of the folding drum 230. In certain embodiments, the folding drum 230 may be configured as a commonly known vacuum drum (i.e., drum that is configured to apply vacuum/suction at one or more portions of its surface). Additionally or alternatively, one or more portions of the article 125 (e.g., the middle portion) may be mechanically secured to the surface 231 of the folding drum 230, for example, with movable bifold clamps such as those described in copending U.S. Ser. Nos. 12/203,339 and 13/051,210. As the folding drum 230 continues to rotate, the absorbent article 125 continues to be transferred from the transfer apparatus 260 to the folding drum 230 until the entire absorbent article 125 is disposed on the folding drum 230. The absorbent article 125 may be disposed on the folding drum 230 such that a first portion of the article (e.g., the leading end portion 150) is disposed on a first protrusion 233 ("leading protrusion"), the middle portion of the absorbent article 125 including the slack 151 is disposed in the pocket 234 adjacent the leading protrusion, and a third portion of the disposable article (e.g., the trailing end portion 155) is disposed on a second protrusion 233 ("trailing protrusion"). It is believed, without being limited by theory, that providing slack 151 in the article 125 is important for facilitating transfer of the middle portion of the article 125 to the pocket 234. For example, in conventional processes, where an article is typically transferred to the folding drum with no slack (i.e., in an extended flat out configuration), the article may extend at least partially over the pocket like a cover instead of being desirably position within the pocket 234. Since the folding drum 230 typically rotates continuously, a leading protrusion may include both the leading end 150 of one article and the trailing end of another article 125. Thus, it may be desirable to provide a suitable space 236 between the leading edge 150 of a first absorbent article 125a and the trailing edge 155 of a second absorbent article 125b (e.g., between 1 and 200 mm apart; 2 and 100 mm; 5 and 80 mm; or even between 10 and 50 mm) which are disposed on the same protrusion 233, as shown in FIG. 6. The transfer apparatus may be configured to provide suitable spacing between the articles 125, for example, as described in copending U.S. Ser. No. 61/364,626, titled Method and Apparatus For Transferring Articles of Different Sizes, filed Jul. 15, 2010 by Yamamoto, et al.

Figure 7A:
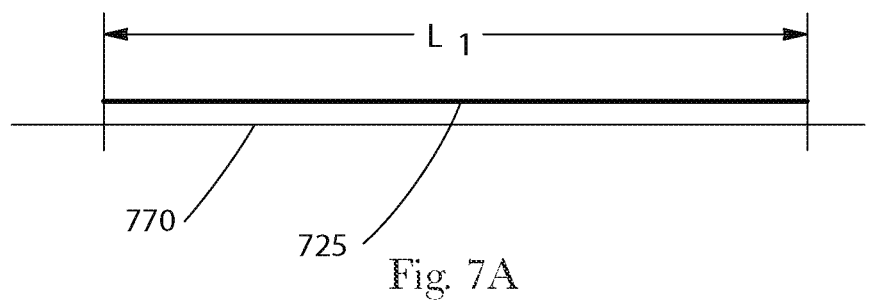
FIGS. 7A and 7B are cross-section views of an article supported on a surface.
Figure 7B:
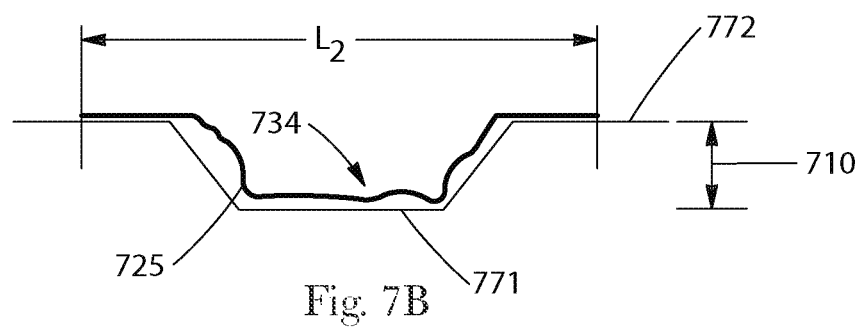

By providing a folding drum 230 with pockets 234, a portion of the absorbent article 125 (e.g., the middle portion) may include slack 151 that can be desirably positioned in the pocket 234, thereby reducing the distance between the leading end edge 256 and the trailing end edge 254 and effectively reducing the length of the article 150. Thus, the length of an article can be adjusted to match the pitch of the drum, which may eliminate the need to replace the drum when manufacturing articles of different lengths. FIGS. 7A and 7B illustrate how placing a portion of an article in a pocket may reduce the overall length of the article being supported on a surface. FIG. 7A shows an article 725 disposed on a flat surface 770. The article 725 has a length $L_1$, which is disposed entirely on the flat surface 770. FIG. 7B shows the article 725 of FIG. 7A disposed on a surface that includes a pocket 734 having a depth 710. As can be seen in FIG. 7B, part of the article 725 is disposed on an outer surface portion 772 and part of the article 725 is disposed in the pocket 734 on the inner surface portion 771. Thus, the length $L_2$ of the article 725 disposed on the outer surface 772 shown in FIG. 7B is less than the length $L_1$ of the article disposed on the surface 700 shown in FIG. 7A, by up to two times the depth 710 of the pocket 734 or more. For example, if the pocket has a depth of 60 mm, the length $L_2$ of the article 725 supported on the outer surface 772 may be up to 120 mm less than the length $L_1$ of the article disposed on the flat surface 770.

After the article 125 is transferred to the folding drum 230, the leading end 150 of the article 125, which is disposed on a protrusion 233, may be carried toward the peel conveyor assembly 245. The peel conveyor assembly 245 may include a vacuum conveyor 245 with a movable surface 232. The folding drum 230 and the peel conveyor assembly 245 may be positioned to provide a suitable distance between the surface 231 of the folding drum 230 and the movable surface 232 of the peel conveyor assembly 245 such that an article 225 disposed on the surface 231 of the folding drum 230 can pass by the peel conveyor surface 232 with little or no resistance. For example, as the trailing end 254 of the article 125 approaches the peel conveyor assembly 245, the trailing end 254 may pass by or even come into contact with the movable surface 232, as long as the contact does not substantially impede the advancement of the absorbent article 125 in the MD. In certain embodiments, the peel conveyor assembly 245 may be configured to peel or remove at least a portion of the leading end 150 of the absorbent article 125 from the outer surface 231 of the folding drum 230 at the third speed $V_3$ (i.e., the speed at which the leading end 150 is travelling) and slow the leading end 150 to a fourth speed $V_4$ (i.e., $V_3 < V_4$).

The peel conveyor assembly 245 may transfer the leading end 150 to the folding conveyor assembly 270 at the fourth speed $V_4$. In certain embodiments, the speed and/or direction of the folding conveyor 270 may be adjusted to match the speed and/or direction of the peel conveyor 245 when the leading end 250 is transferred. For example, the movable surface 280 of the folding conveyor assembly 270 may be travelling in the same direction (i.e., away from the folding drum 230) and at substantially the same speed (e.g., within 1%, 2%, 3%, 4%, or even 5%) as the movable surface 232 of the peel conveyor assembly 245. In this example, after the leading end 250 is transferred to the folding conveyor assembly 270, the direction and/or speed of the movable surface 280 of the folding conveyor 270 may be changed such that the leading end 250 is carried back toward the folding drum at the first speed $V_1$. The folding conveyor assembly 270 may include a vacuum conveyor 270a with a movable surface 280. The folding drum 230 and the folding conveyor assembly 270 may be positioned to provide a suitable distance between the surface 231 of the folding drum 230 and the movable surface 280 of the folding conveyor assembly 270 such that an article 225 disposed on the surface 231 of the folding drum 230 can pass by the folding conveyor surface 280 with little or no resistance. The folding conveyor assembly 270 may accelerate the leading end 150 to, e.g., the third speed $V_3$ and transfer the leading end 150 back to the folding drum 230. In this way, the leading end 150 and the trailing end 155 may be traveling at substantially the same speed when the two portions 150, 155 are brought together in a face-to-face relationship to provide a folded article 125c. The folded article 125c may then be subjected to one or more additional, optional processes such as a commonly known process for permanently and/or refastenably joining the front and back side panels of the article 125 to one another to form a disposable pant or a pre-fastened disposable pant. Exemplary methods for seaming, inspecting, and tucking an article to form a pre-fastened pant are disclosed in U.S. Pat. No. 6,888,143, issued to Vogt, et al.

Figure 8:
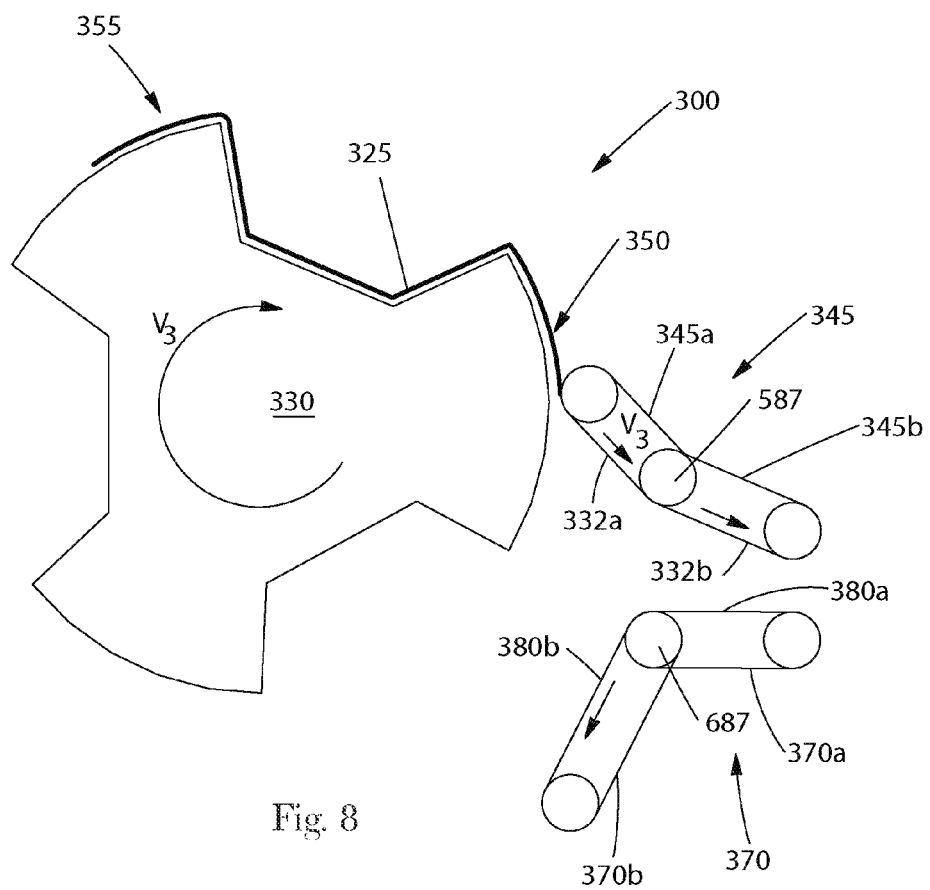
FIGS. 8-12 are schematic views of an embodiment of the method and apparatus disclosed herein.

FIG. 8 shows an exemplary embodiment of a folding system 300 that includes a rotatable folding drum 330, a peel conveyor assembly 345 and a bifold conveyor assembly 370. The folding drum 330 may be configured as one or more of the folding drums described hereinabove as long as it includes a surface for carrying an article 325. The peel conveyor assembly 345 may include a first peel conveyor 345*a* and a second peel conveyor 345*b*, and each peel conveyor 345*a*, 345*b* may include a movable surface 332*a*, 332*b*. For example, the first and/or second movable surface 332*a*, 332*b* of the peel conveyor assembly 345 may include a movable foraminous conveyor belt configured in an endless loop. In certain embodiments, the first peel conveyor movable surface 332*a* may move at a single speed, while the second peel conveyor movable surface 332*b* may be configured to travel at the same speed as the first movable surface 332*a* and at one or more slower second speeds, including a speed of zero. In other embodiments, the first and second peel conveyor movable surfaces 332*a*, 332*b* may both be configured to move at two or more speeds. In certain embodiments, the first and second peel conveyors 345*a* and 345*b* may share one or more common elements such as, for example, a shaft 587. Shaft 587 may be coupled to, e.g., a constant or variable speed motor and configured to drive the endless belt 332*b* of the second peel conveyor 345*b* at one or more speeds. The shaft 587 may also include one or more free-spinning rollers or pulley-like elements that enable the shaft 587 to simultaneously operate as an idler roll for the endless belt 332*a* of the first peel conveyor 345*a*. By sharing shaft 587, the first and second peel conveyors 332*a* and 332*b* may be configured to overlap at one end in the machine direction, and thereby facilitate transfer of an article from the first peel conveyor 345*a* to the second peel conveyor 345*b*. While the first and second conveyors 345*a*, 345*b* in the foregoing example may share a common element, it is to be understood that the first and second conveyors 345*a*, 345*b* may also be configured as discrete components.

The bifold conveyor assembly 370 may include a first bifold conveyor 370*a* and a second bifold conveyor 370*b*. The first and second bifold conveyor 370*a*, 370*b* may each include a movable surface 380*a*, 380*b* for receiving an article from the peel roll assembly 245 and securely carrying it back toward the folding drum 330. The first and second bifold conveyors 370*a*, 370*b* may be configured to share one or more common elements such as, for example, a shaft 687. Shaft 687 may be coupled to, e.g., a variable speed drive motor and configured to drive the endless belt 380*a* of the first bifold conveyor 370*a* at one or more speeds. The shaft 687 may also include one or more free-spinning rollers or pulley-like elements that enable the shaft 687 to simultaneously operate as an idler roll for the endless belt 380*b* of the second bifold conveyor 370*b*. The second bifold conveyor 370*b* may be driven by, e.g., a constant speed motor that drives the second bifold conveyor belt 380*b* at, e.g., the surface speed of the folding drum 330, through a mechanical coupling. By sharing shaft 687, the first and second bifold conveyor belts 380*a*, 380*b* may be configured to overlap at one end in the machine direction, and thereby facilitate transfer of an article from the first bifold conveyor 370*a* to the second bifold conveyor 370*b*. While the first and second bifold conveyors 370*a*, 370*b* may share a common element, it is to be understood that the first and second bifold conveyors 370*a*, 370*b* may also be configured as discrete components. It is also to be appreciated that, in certain embodiments, the second conveyor 370*b* may also be configured as a variable speed conveyor.

Figure 9:
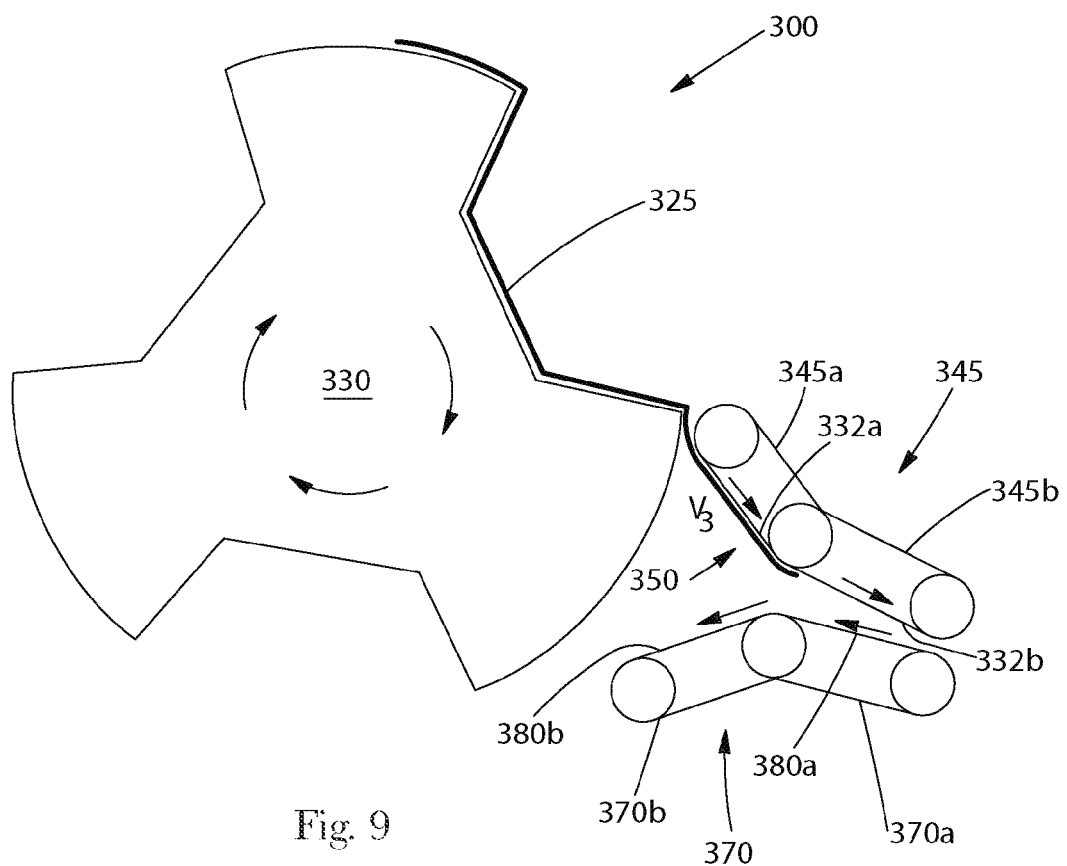

Referring to FIGS. 8-12, an exemplary process for folding an article with the folding system 300 is described. As shown in FIG. 8, the folding drum 330 rotates to position the leading end 350 of the article 325 proximate the peel conveyor assembly 345 at speed $V_3$. Thus, in certain embodiments, it may be desirable to configure the movable surface 332*a* of the first peel conveyor 345*a* to travel at or approximately speed $V_3$. As the leading end 350 of the article 325 approaches the peel conveyor assembly 345, at least a portion of the leading end 350 may be transferred and secured to the movable surface 332*a* of the first peel conveyor 345*a*, as shown in FIG. 9. Any force exerted by the folding drum 330 on the leading end 350 (e.g., suction/vacuum/mechanical) may be simultaneously or sequentially removed or reduced as the leading end 350 is peeled from the folding drum 330. After receiving the leading end 350 of the absorbent article 325 from the folding drum 330, the first peel conveyor 345*a* transports the leading end 350 towards the movable surface 332*b* of the second peel conveyor 345*b* and transfers it thereto. At the time of transfer, the speed of the second peel conveyor 345*b* may substantially match the speed of the first peel conveyor 345*a* (e.g., speed $V_3$). But after at least a portion of the leading end 350 has been transferred to the second peel conveyor 345*b*, the speed of the second peel conveyor 345*b* may be decreased to a second slower speed $V_4$, in preparation for transferring the leading end 350 of the article 325 to the bifold conveyor assembly 370.

Once the leading end 350 reaches a particular portion of the peel conveyor assembly 345 (e.g., at or near the end of the second peel conveyor 345*b*) and/or reaches a desired speed (e.g., $V_4$), the leading end 350 may be transferred to the bifold conveyor assembly 370. In preparation for the transfer, the first bifold conveyor surface 380*a* and/or the second peel conveyor surface 332*b* may be slowed or even temporarily stopped prior to, during, and/or after engagement of the leading end 350 by the first bifold conveyor surface 380*a*. Upon engaging the leading end 350, the bifold conveyor assembly 370 may be configured to apply sufficient vacuum (i.e., suction) to the leading end 350 to overcome the force holding the leading end 350 to the peel conveyor assembly 345. In certain embodiments, it may be desirable to reduce or remove the suction exerted by the peel conveyor assembly 345 on the absorbent article 325 or portions thereof when the absorbent article 325 reaches a desired position or when the bifold conveyor assembly 370 engages the leading end 350.

In some instances, the first bifold conveyor surface 380*a* may be traveling in substantially the opposite direction as the second peel conveyor surface 332*b*. Thus, in order to reduce the possibility of such premature engagement or contact of the first bifold conveyor 370*a* with the second peel conveyor 332*b* and/or leading end 350, a suitable distance or gap may be provided between the second peel conveyor surface 332*b* and the first bifold conveyor surface 380*a*. In certain embodiments, one or both of the movable surfaces 380*a*, 380*b* of the bifold conveyor assembly 380 may be repositionable relative to the peel conveyor assembly 345 and/or folding drum 330 via a positioning mechanism mechanically coupled to the bifold conveyor assembly 370. Similarly, in certain embodiments, one or both of the movable surfaces 332*a*, 332*b* of the peel conveyor assembly 345 may be repositionable relative to the bifold conveyor assembly 370 and/or folding drum 330 via a positioning mechanism mechanically coupled to the peel conveyor assembly 345. A suitable positioning mechanism may be configured to automatically vary the distance between the first movable surface 380*a* of the bifold conveyor assembly 370 and the second movable surface 332b of the peel conveyor assembly 345 in a continuous or intermittent fashion. Such positioning mechanisms may include for example, one or more cams, pistons, gears, pulleys, and the like. The positioning mechanism may be configured to suitably position the first bifold conveyor 370a to engage the leading end 350 during the "upstroke" (i.e., when the movable surface 380a of the first vacuum conveyor 370a is being moved closer to the movable surface 332b of the second conveyor 345b) and to provide a suitable gap between the vacuum conveyor 380 and the peel conveyor 345 during the "downstroke" (i.e., when the movable surface 380a of the first vacuum conveyor 370a is being moved away from the movable surface 332b of the second conveyor 345b), as suitably exemplified in copending U.S. Ser. No. 61/322,333. Additionally or alternatively, the position of the movable surface 332b of the second conveyor 345b may be moved relative to the movable surface 380a of the first conveyor 370a. The positioning mechanism may have any suitable stroke length desired, for example, a stroke length of greater than 1 mm, between 1 mm and 20 cm, 1 mm and 20 mm, 1 mm and 10 mm, or even 1 mm and 5 mm, which provide a gap distances that is at least greater than the thickness of the absorbent article 325, for example, greater than 1 mm, between 1 mm and 20 cm, or even between 1 mm and 20 mm. One particularly suitable example for providing a gap includes using a cam with a 3 mm stroke length to continuously varying the position of the first bifold conveyor surface 380a relative to the second peel conveyor surface 332b. In certain embodiments, it may be desirable to vary or hold constant the distance between the surface 331 of the folding drum 330 and one or more of the movable conveyor surfaces 332a, 332b, 380a, 380b. In certain embodiments, the movement of the first bifold conveyor 370a may pause at a particular position during the bifold process, for example, at the "top of the upstroke" (i.e., when the distance between the first bifold conveyor surface 380a and the second peel conveyor surface 332b is at a minimum), the "bottom of the downstroke" (i.e., when the distance between the first bifold conveyor surface 380a and the second peel conveyor surface 332b is at a maximum), and/or upon engaging the leading end 350. In a particularly suitable embodiment, the first bifold conveyor 370a may pause at the top of the upstroke with simultaneously engaging the leading end 350.

Figure 10:
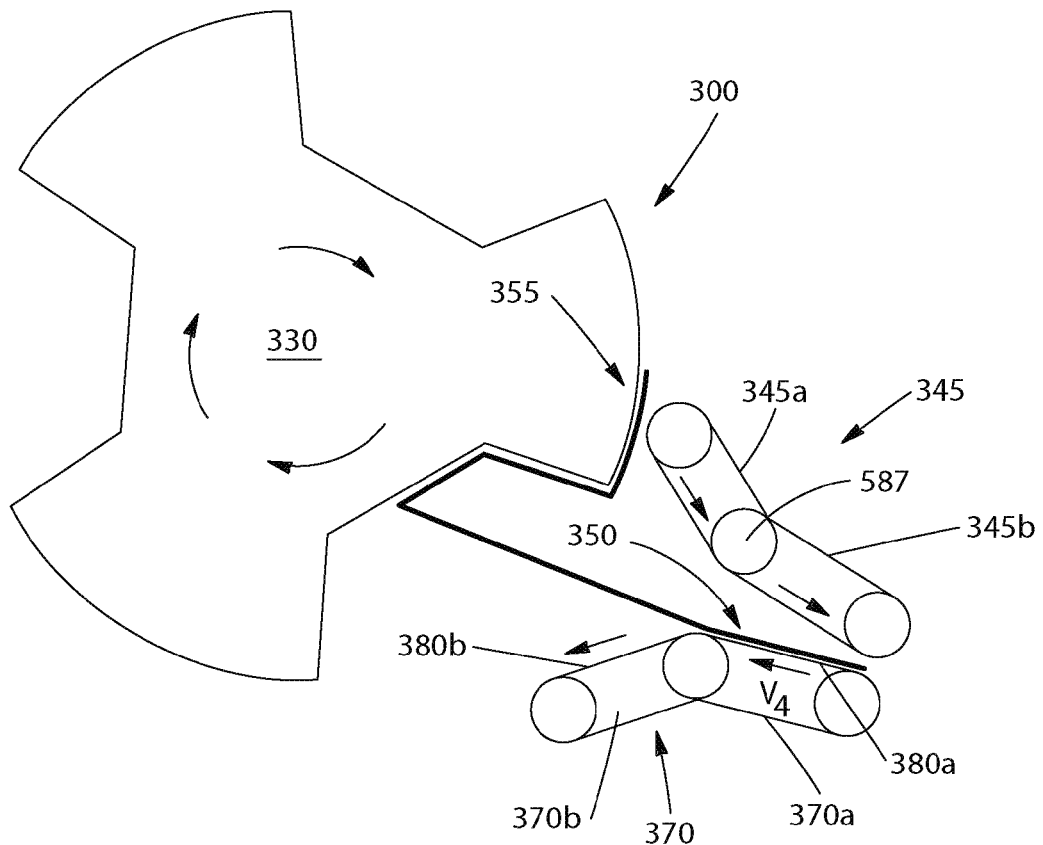
Figure 11:
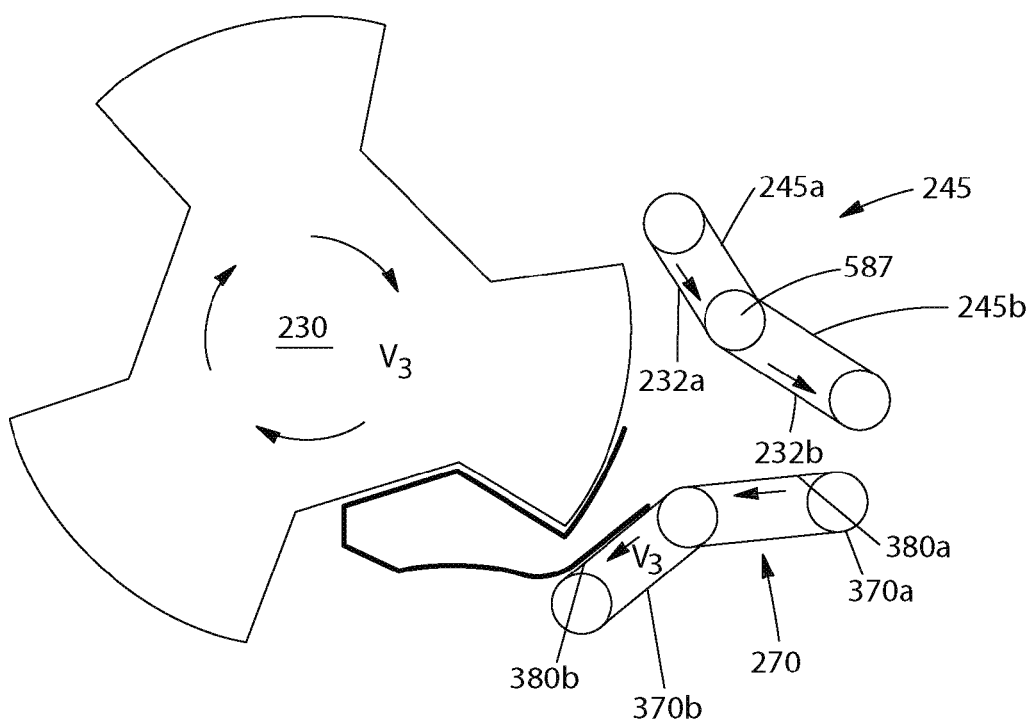
Figure 12:
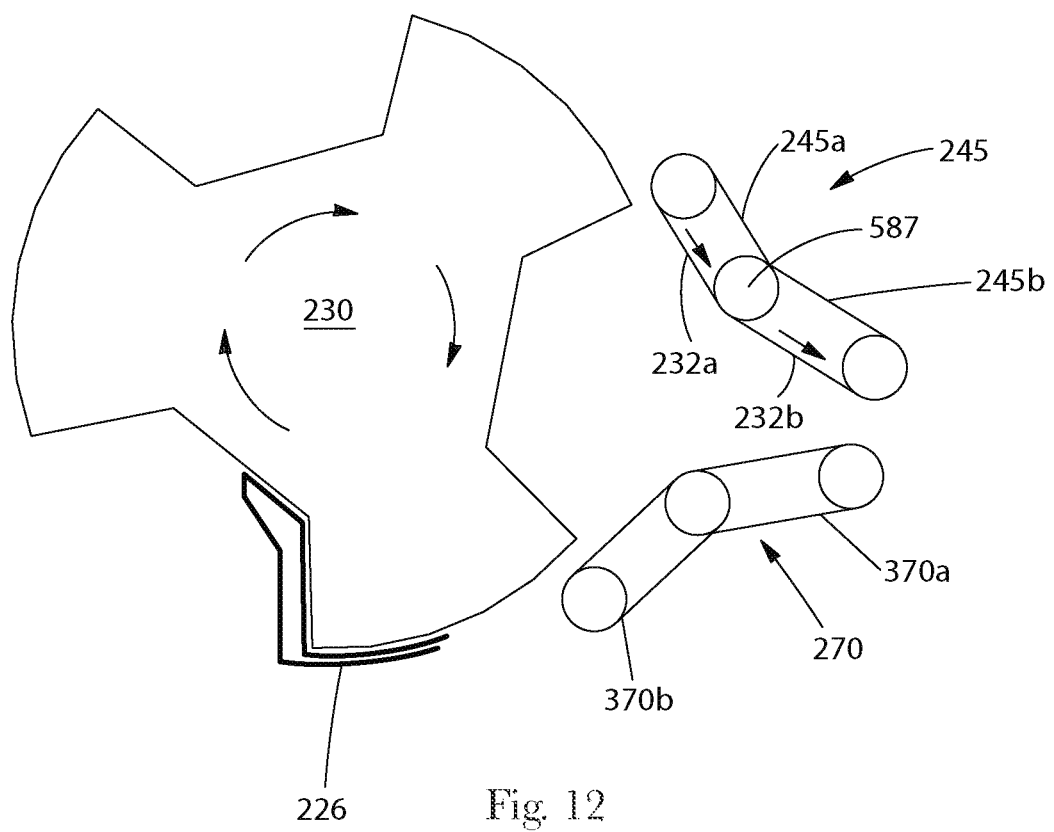

As shown in FIG. 10, once the leading end 350 has been transferred to the bifold conveyor assembly 370, the bifold conveyor assembly 370 accelerates the leading end 350 back to the third speed $V_3$ and carries it back towards the folding drum 330 to be placed in a face-to-face relationship with the trailing end portion 355. The leading end 350 is received by the movable surface 380a of the first bifold conveyor 370a at speed $V_4$ and accelerated to speed $V_3$. The leading end 350 is then be transferred to the moving surface 380b of the second bifold conveyor 270b, which is moving at speed $V_3$ toward the folding drum 330, as shown in FIG. 11. As shown in FIG. 12, the leading end 350 is transferred from the second bifold conveyor 370b back to the folding drum 330 to provide a bifolded article 226, which can then be subjected to additional, optional process such as adhesive and/or high pressure bonding or pre-fastening, for example, to form a pant product.

In certain embodiments, the first and second movable surfaces 380a and 380b may each be driven by a variable speed motor. In this example, after engaging the leading end 350, the movable surface 380a of the first bifold conveyor 370a may be accelerated to a fifth speed $V_5$ that is faster than the fourth speed $V_4$ but slower than the third speed $V_3$ (i.e., the speed at which the trailing end of the article is travelling). Continuing with this example, the second bifold conveyor 370b may accelerate the leading end 350 from the fifth speed $V_5$ to the third speed $V_3$. In this way, the leading end 350 and the trailing end 355 may be traveling at substantially the same speed when the two portions 350, 355 are brought together in a face-to-face relationship.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for folding an article; the method comprising:
   transferring a leading end portion of the article from a first carrier moving at a first speed to a movable surface of a first transfer apparatus moving at the first speed, and slowing the leading end portion to a second speed such that slack is formed in the article;
   transferring a trailing end portion of the article to the moving surface of the first transfer apparatus at the first speed;
   accelerating the leading end portion of the article to a third speed that is greater than the first speed;
   accelerating the trailing end portion of the article to the third speed;
   transferring the article to a rotating folding drum moving at the third speed, the folding drum comprising at least one pocket and at least one protrusion;
   transferring the leading end portion of the article to a movable surface of a second transfer apparatus, and slowing the leading end portion to a fourth speed;
   transferring the leading end portion of the article to a movable surface of a third transfer apparatus, and accelerating the leading end portion to the third speed;
   transferring the leading end portion to the folding drum at the third speed such that the leading end portion and the trailing end portion are arranged in a face-to-face relationship to form a folded article.

2. The method of claim 1, further comprising joining the leading end portion and the trailing end portion together.

3. The method of claim 2, wherein the leading end portion and the trailing end portion are at least one of permanently joined and refastenably joined.

4. The method of claim 2, wherein the article is a disposable absorbent article comprising a first waist region corresponding to the leading end portion, a rear waist region corresponding to the trailing end portion, the waist regions each including at least one fastener, wherein the fasteners of the waist regions are joined together to form a pre-fastened pant.

5. The method of claim 1, wherein the leading end portion is transferred to a first protrusion on the folding drum.

6. The method of claim 5, wherein the trailing end portion is transferred to a second protrusion on the folding drum.

7. The method of claim 6, wherein the slack is disposed in a pocket between the first and second protrusions.

8. The method of claim 1, wherein the protrusion defines an outer surface of the folding drum and wherein the article comprises opposing end edges, a distance between the opposing end edges as measured on the outer surface of the folding drum being less the distance between the opposing end edges when the article is in a flat-out configuration.

9. The method of claim 8, wherein the distance is at least about 10% less.

10. The method of claim 1, wherein the second transfer apparatus includes a first vacuum conveyor and a second vacuum conveyor.

11. The method of claim 10, wherein the first vacuum conveyor is positioned proximate to a surface of the folding drum and receives the leading end portion therefrom at the third speed, the first vacuum conveyor transferring the leading end portion to the second vacuum conveyor at the third speed, the second vacuum conveyor decelerating the leading end portion to the fourth speed.

12. The method of claim 10, wherein the first and second vacuum conveyors share a common element.

13. The method of claim 1, wherein the third transfer apparatus includes a third vacuum conveyor and a fourth vacuum conveyor.

14. The method of claim 12, wherein the third vacuum conveyor is positioned proximate to the movable surface of the second transfer apparatus and receives the leading end portion therefrom at the fourth speed, the third vacuum conveyor accelerating the leading end portion to the third speed, and transferring the leading end portion to the fourth vacuum conveyor at the third speed, the fourth vacuum conveyor transferring the leading end back to the folding drum at the third speed.

15. The method of claim 12, wherein the third and fourth vacuum conveyors share a common element.

16. The method of claim 1, wherein at least one of the second and third transfer apparatuses can be repositioned to vary the distance between the movable surface of the second transfer apparatus and the movable surface of the third transfer apparatus.

17. The method of claim 1, wherein the fourth speed is zero.

18. The method of claim 1, wherein the leading and trailing end portions are aligned in the face-to-face configuration.

19. The method of claim 12, wherein a first set of belts transfers the leading end portion of the article from the first carrier to the folding drum, and a second set of belts transfers the trailing end portion of the article from the first carrier to the folding drum.

* * * * *